United States Patent [19]

Preti

[11] 4,182,039
[45] Jan. 8, 1980

[54] ARTICULATOR WITH BITE PLATE GUIDES

[76] Inventor: Giulio Preti, Str. Costalunga 10/2, Moncalieri, Italy

[21] Appl. No.: 735,342

[22] Filed: Oct. 26, 1976

[30] Foreign Application Priority Data

Oct. 31, 1975 [IT] Italy ............................. 69693 A/75

[51] Int. Cl.² ............................................ A61C 11/00
[52] U.S. Cl. ..................................................... 433/54
[58] Field of Search ...................... 32/32; 248/124, 125

[56] References Cited

U.S. PATENT DOCUMENTS

| | | | |
|---|---|---|---|
| 1,322,386 | 11/1919 | Wilson | 32/32 |
| 1,362,602 | 12/1920 | Coble | 32/32 |
| 1,550,339 | 8/1925 | Branson et al. | 32/32 |
| 1,780,308 | 11/1930 | Morris | 248/124 |
| 2,018,679 | 10/1935 | Lawson | 32/32 |
| 2,334,643 | 11/1943 | Moore | 32/32 |
| 2,801,470 | 8/1957 | Logan et al. | 32/32 |
| 2,884,696 | 5/1959 | Bonfanti | 32/32 |
| 3,577,640 | 5/1971 | Lee | 32/32 |

FOREIGN PATENT DOCUMENTS 845232 6/1952 Fed. Rep. of Germany ............. 32/32

Primary Examiner—Russell R. Kinsey
Assistant Examiner—John J. Wilson
Attorney, Agent, or Firm—Beveridge, De Grandi, Kline & Lunsford

[57] ABSTRACT

Procedure and device, through which it is possible to realize a three-dimensional and transparent representation of the crest of each plater mold, and then to displace this representation, while keeping it parallel to its original position, in a direction at least approximately perpendicular to the occlusal plane, thus translating to an occlusal level under a three-dimensional form, the characteristics of the anatomic conformation of the underlying alveolar crests. Therefore, even after the application of a wax mask over the plaster mold, we still dispose of a representation of the crest, so displaced by perpendicular translation as to leave free the space needed for the fitting of the teeth, and this representation will allow in every moment to select the position of the different teeth and to control the position assigned, singularly and collectively, to the teeth themselves.

5 Claims, 9 Drawing Figures

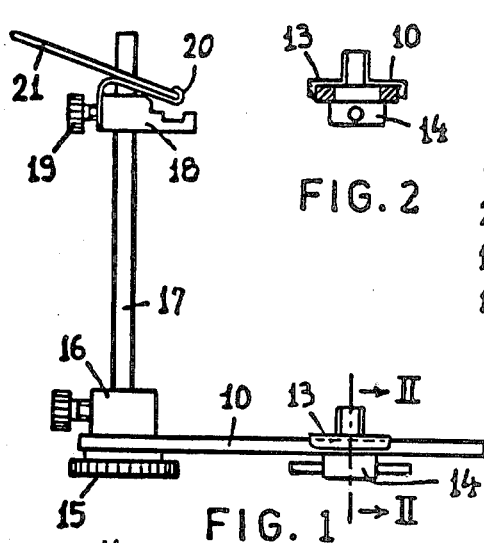
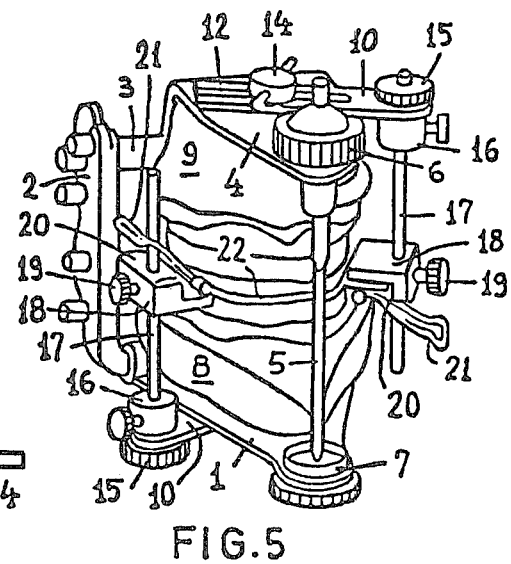
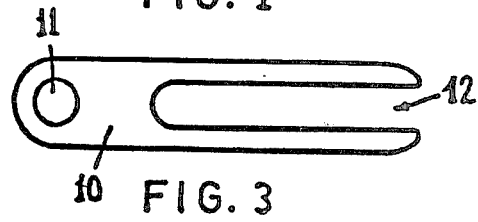
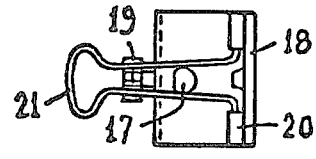
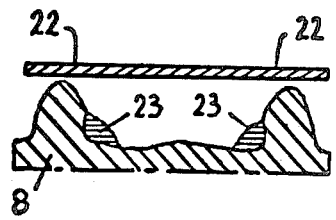
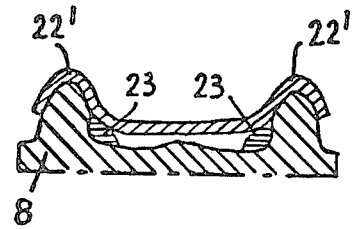
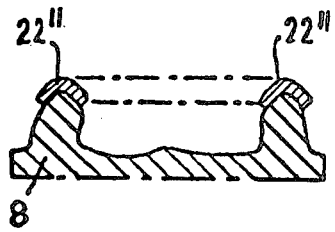
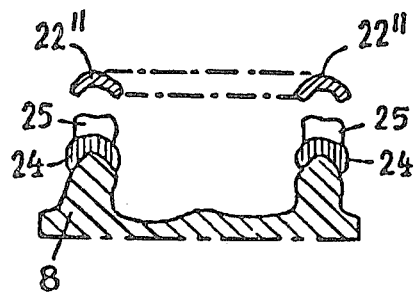

ARTICULATOR WITH BITE PLATE GUIDES

The object of the present invention is a device applied in the context of a procedure-which is also part of the present invention—allowing a better rationalization of the possibility of checking the precise execution of the fitting operation immediately thereafter.

In the fitting of the back teeth (premolars and molars) in a total prosthesis we are confronted with the problem of giving to this prosthesis a satisfactory stability during the process of mastication, from which depends on a large extent the success of the prosthetic operation. In order to achieve a satisfactory stability it is necessary, among other things, to compensate the inclined destabilizing planes both on the frontal and on the sagittal plane. To this end, as each tooth is fitted-in we must keep in account the conformation of the underlying alveolar crest, represented three-dimensionally by a mould of plaster which is mounted in the right operational position with respect to the mould related to the alveolar crest of the other jaw, into an articulating device on which the fitting is done.

For this fitting we form a wax mask on the crest of the mold, and in this mask we introduce the teeth in the position we deem correct; the semi-finished product thus obtained is them submitted to the successive operations whereby the final prosthesis is achieved. Nevertheless, the existence of the plaster mold does not allow the observation of the crest where the fitting of each tooth is done; therefore the fitting operation must be determined by the operator on the basis of measurements of difficult execution, or on the basis of his own talent and experience, fraught anyhow with the acceptance of relatively ample approximations. In addition, after the fitting is finished, it will not be possible to control directly the right position of the tooth with respect to the anatomic conformation of the alveolar crest represented by the mold covered with the wax mask.

It is the purpose of the present invention to rationalise this fitting operation of the teeth in the total prosthesis, rendering the precision of the results independent of the subjective skill of the operator and allowing a continuous control of the operation both during its execution and after it is completed. This possibility of checking must therefore represent a guide for the execution during the fitting-in of the teeth and an efficient means for checking the results achieved thereafter.

According to the invention, this purpose can be attained by providing a procedure and a device through which it is possible to realize a three-dimensional and transparent representation of the crest of each plaster mold, and then to displace this representation, while keeping it parallel to its original position, in a direction at least approximately perpendicular to the occlusal plane, thus translating to an occlusal level under a three-dimensional form the characteristics of the anatomic conformation of the underlying alveolar crests. Therefore, even after the application of a wax mask over the plaster mold, we still dispose of a representation of the crest, so displaced by perpendicular translation as to leave free the space needed for the fitting of the teeth, and this representation will allow in every moment to select the position of the different teeth and to control the position assigned, singularly and collectively, to the teeth themselves. The device which renders easy and precise this operation comprises a small plate destined to be fixed solid with the articulator, a bar having a non-round section mounted perpendicularly onto said plate, said bar being rotatable and apt to be blocked in any chosen position, and a small clamp mounted on this bar, which can slide all over the bar's length without rotating and can be blocked in any selected position. This clamp is destined to receive and to hold a plate of a transparent, moldable and heat-softening material, said plate being suited to be formed against the plaster-mold crest already positioned on the mentioned plate of the articulator to be thereafter displaced in such a direction as to be kept in a position parallel to the original one by sliding along the bar which supports it.

For a clearer understanding of the invention there is thereafter given the following description of an embodiment, which is a non-limiting example, and represented under a schematic form in the adjoined drawing, where:

FIG. 1 is a view in side elevation of a device as that of the invention,

FIG. 2 shows a section made along the line II—II of FIG. 1,

FIGS. 3 and 4 show in a plane respectively the base plate and the plate-retaining clamp.

FIG. 5 shows in a schematic form an articulator equipped with two of the devices forming the basis of the invention, FIGS. from 6 to 9 illustrate in a schematic form four stages of the procedure which is part of the invention.

An articulating device destined to receive the application of the devices according to the invention is composed generally of a lower plate 1 joined to posts 2, with respect to which a shaft 3, solid with the upper plate 4, is mounted. Suitable regulating means, which will be omitted here since they do not concern the invention, allow the reproduction through the complex of the articulating conditions of the patient's jaw to which the prosthesis being built is destined. A stylus 5, borne by the upper plate 4 through the regulating means 6 and opposed to a seat 7 borne by the lower plate 1 defines the condition of occlusion.

In the known fashion the plaster mold 8 of the alveolar crest related to the jaw of the patient is fixed on the lower plate 1. Similarly the plaster mold 9 of the alveolar crest related to the upper jaw of the patient is fixed to the upper plate 4. Thanks to the application of the known procedure in this branch, the reciprocal relationships of these molds will reproduce the alveolar relationships between the opposed alveolar crests of the patient.

The device forming the object of the invention comprises a small base plate 10 presenting a perforation 11 for the anchorage at one end and, along the axis of the small plate, an open slit 12. A small U-shaped plate 13 works together with the plate 10, the former having the function of assuring a level resting position and of preventing a straddling of the plate under the clamping stresses. A two-step winged screw 14 allows to fix the base plate 10 to the plate 1 or to the plate 4 of an articulator and, at the same time, to fix in the known way the plaster molds 8 and 9 to said plates. This is valid for the types of articulators where the molds are fixed to the plates through screws. If we intend to use the device of the invention with other types of articulators, the end of the plate 10 bearing the anchorage perforation 11 will be placed in contact with the respective plate of the articulator and it will be fixed there by incorporating it in the mass of plaster being cast therein. Inside the anchorage perforation 11 there is fixed through a screw, in a position suited to be regulated by rotation, a stator 16 bearing a bar 17 with a non-round section extending in a direction perpendicular to the plane of the plate 10. In the named case, where the plate is incorporated into a mass of plaster rather than fixed to the articulator by a screw, the stator 16 is instead fixed, eventually with the help of the plate 13, in a conveniently selected position of the slit 12. The two named assembling ways allow the use of the device on every type of articulator.

On the bar with non-round section, whose section can be conveniently that of a circular segment limited by a flattening or of a polygon or the like, there is mounted, slidable but not rotatable, a clamp composed of a block 18 which can be fixed along the bar 17 through a pressure screw 19 acting on the flat side of the bar, by an elastic steel jaw and by a releasing lever 21.

Inside this clamp 18–21 there can be locked a point of the border of a plate 22 made of transparent, heat-moldable material. Such plates are available from the trade of the different items for the dental techniques, under the denomination of "transparent base plates". Thanks to the described structure, it is clear that the plate 22 will be substantially parallel to the plate of the articulator to which the device is fixed and that it can be displaced, still keeping a position parallel to the initial one, along the direction of the bar 17, and fixed to any chosen position on the length of the same. In the case of a more general application of the device, two devices like the former are joined to two plates of an articulator, as is shown in FIG. 5. The use of the device takes place as follows: The moldable plate 22 borne by the clamp 18–21 is initially placed in the vicinity of the crest of the mold on which we are working, for instance the lower mold 8 in FIG. 6. The plate 22 is then heated to molding temperature, for instance by directing upon it the flame of a Bunsen burner. After the plate has reached its softening point, it is pressed against the crest of the plaster mold, using for instance a mass of "moldina", so as to make it to adhere to the mold at least in the crest regions, thus assuming the corresponding shape 22', as shown in FIG. 7.

Since we are not interested - neither would it be possible -to reproduce the under-ribs of the mold, these can be previously leveled off with a mass of "moldina" 23. In those zones which are out of our interest the shaped plate 22 can remain at a distance from the mold, while in the case of an imperfect adhesion in the regions of the crest there can be introduced corrections by heating up and shaping further the corresponding section of plate 22'.

After molding, plate 22' is made to slide off the bar 17 together with the clamp 18–21, which is solidly connected to it, and is finished by removing the excess and those parts which are of no interest, and burring it when necessary. After this it is reduced to the sole representation 22" of the zones concerning the crest of the mold and can be placed back in its position (FIG. 8). It is also possible to write, with a pen or the like, any remark concerning the fitting of the teeth, such as the crest line, the zone of the highest masticatory resistance, the sloping line and so on, which can be clearly seen from the still exposed mold.

This three-dimensional and transparent representation, with the remarks of the alveolar crest written thereupon, is then again taken away.

After the application of the wax mask 24 on the crest of the mold 8, the named representation 22" of the alveolar crest can be put back in the apparatus, placed at the same or above the occlusal level, and the teeth 25 can be introduced into the wax mask observing both the three-dimensional representation of the underlying alveolar crest, supplied by the shaped plate 22" and all the useful notes written upon it, thus in the most efficient and dependable way. Besides, once finished the assembling, the same shaped plate 22" will afford a very efficient means for checking the precision of the finished assembly.

The predisposition of the non-round-sectioned bar 17, working in combination with the clamp 18–21 whose pressure screw works on the flat surface of the bar, warrants the reproducibility of the precise mounting position of the plate and the conservation of the parallel orientation when the same is displaced, with tolerances of the order of 1/10 of a millimeter, thus amply sufficient for the purpose. The device and the procedure according to the invention assure therefore a guide and the possibility of checking the fitting of the teeth in total prostheses, whereby it is possible to reach a greater precision in the assembling with a greater dependability of the results aimed to.

Besides, the required degree of precision can be assured independently of the skill and experience of the operator. Therefore the device finds its principal applications in a systematic use by the less experienced operator and, in cases presenting particular difficulties, with reference to the anatomic conformation of the alveolar crests and to their incongruence, also by the more experienced operator. It is of course possible to introduce several modifications to the details both of the components of the device and to the isolated operations of the procedure, such as those were described in an embodiment of the invention, without thereby departing from the concept of the invention and from the range of the present patent.

I claim:

1. A device for guiding and checking the fitting of teeth in total dental prostheses comprising an articulating device adapted to bear a plaster mold; a first base plate fixed to the articulating device; a second base plate fixed to the articulating device; a first bar member having a non-circular cross-section; first mounting means mounting the first bar member to extend substantially perpendicular to the first base plate while permitting rotation of the first bar member around the first bar member axis and fixing of the first bar member in any rotational position thereof; a first clamp adapted to hold a moldable transparent plate and mounted on the first bar member for sliding movement therealong without rotational movement of the first clamp relative to the first bar member, while permitting fixing of the first clamp at any position along the first bar member; a second bar member having a non-circular cross-section; second mounting means mounting the second bar member to extend substantially perpendicular to the second base plate while permitting rotation of the second bar member around the second bar member axis and fixing of the second bar member in any rotational position thereof; and a second clamp adapted to hold a moldable transparent plate and mounted on the second bar member for sliding movement therealong without rotational movement of the second clamp relative to the second bar member, while permitting fixing of the second clamp at any position along the second bar member.

2. A device as claimed in claim 1 in which each mounting means comprises a stator member rotatably mounted on the associated base plate and mounting associated the bar member for rotation of the bar member about the bar member axis, and a screw for fixing of the bar member in any rotational position thereof.

3. A device as claimed in claim 2 in which each base plate includes a first base plate portion having a perforation and an elongated slit therein, the perforation adapted for mounting of the stator and the elongated slit adapted for fixing the base plate and the articulating device to each other.

4. A device as claimed in claim 3 in which each base plate further includes a U-shaped plate having a perforation therein and cooperating with the first base plate portion of the associated base plate to provide level support of the associated base plate and prevent straddling of the associated base plate under stress, and a winged screw extending across the elongated slit and the perforation to fix the associated base plate to the articulating device.

5. A device as claimed in claim 1 in which each clamp comprises a pressure screw and a perforated block, the perforated block being adapted to be fixed by the pressure screw to the associated bar member and having a jaw portion for holding the moldable transparent plate and means for actuating the jaw portion.

* * * * *